United States Patent
Roffe et al.

(10) Patent No.: US 6,416,320 B1
(45) Date of Patent: Jul. 9, 2002

(54) DENTAL INSTRUMENT FOR USE IN ROOT CANAL OBTURATION

(76) Inventors: Brian Roffe; Tara Roffe, both of 376 Yale Ave., Woodmere, NY (US) 11598-2051

( * ) Notice: Subject to any disclaimer, the term of this patent is extended or adjusted under 35 U.S.C. 154(b) by 15 days.

(21) Appl. No.: 09/642,265

(22) Filed: Aug. 18, 2000

Related U.S. Application Data

(63) Continuation-in-part of application No. 09/359,252, filed on Jul. 22, 1999, now Pat. No. 6,106,283.

(51) Int. Cl.$^7$ ................................................ A61C 3/00
(52) U.S. Cl. ......................... 433/32; 219/223; 219/229
(58) Field of Search ..................... 433/32, 81, 102; 219/223, 226, 229, 231, 481

(56) References Cited

U.S. PATENT DOCUMENTS

| | | | |
|---|---|---|---|
| 1,370,524 A | 3/1921 | Dumaine | 219/223 |
| 3,899,830 A | 8/1975 | Malmin | 32/15 |
| 4,392,827 A | 7/1983 | Martin | 433/32 |
| 4,480,996 A | 11/1984 | Crovatto | 433/164 |
| 4,525,147 A | 6/1985 | Pitz et al. | 433/224 |
| 4,527,560 A | 7/1985 | Masreliez | 433/32 |
| 4,681,545 A | 7/1987 | Lapcevic | 433/224 |
| 4,894,011 A | 1/1990 | Johnson | 433/81 |
| 4,992,045 A | 2/1991 | Beisel | 433/32 |
| 5,043,560 A | 8/1991 | Masreliez | 219/497 |
| 5,067,900 A | 11/1991 | McSpadden | 433/81 |
| 5,215,461 A | 6/1993 | Riazi | 433/224 |
| 5,374,806 A | * 12/1994 | Chou | 219/229 |
| 5,605,460 A | 2/1997 | Heath et al. | 433/224 |
| 5,752,825 A | 5/1998 | Buchanan | 433/32 |
| 5,893,713 A | 4/1999 | Garman et al. | 433/32 |

OTHER PUBLICATIONS

Endotec II, Thermal Condenser for Gutta Percha, Lone Star Technologies, Jan. 6, 2000.

* cited by examiner

*Primary Examiner*—Todd E. Manahan
(74) *Attorney, Agent, or Firm*—Brian Roffe

(57) ABSTRACT

An apparatus for use in obturating a root canal including a first member having a frame, a heatable probe mounted to the frame to project outward from the frame and adapted for insertion into or into proximity of the root canal, and one or more pressure sensors for detecting application of external pressure on the first member. Each pressure sensor is coupled to the heating probe such that the heating probe is heated upon the application of pressure on the first member. A second member covers the heating probe and is attachable to the first member in a position in which it covers the heating probe and movable from that position to expose the heating probe. Another apparatus for use in obturating root canals includes a cylindrical housing having an inwardly depressible region, a heatable probe adapted for insertion into or into proximity of the root canal, and a cradle having a seat in which the heating probe is received. The cradle is arranged inward of the depressible region of the housing and constructed such that depression of the region causes displacement of the cradle and movement of the heating probe in an outward direction.

30 Claims, 8 Drawing Sheets

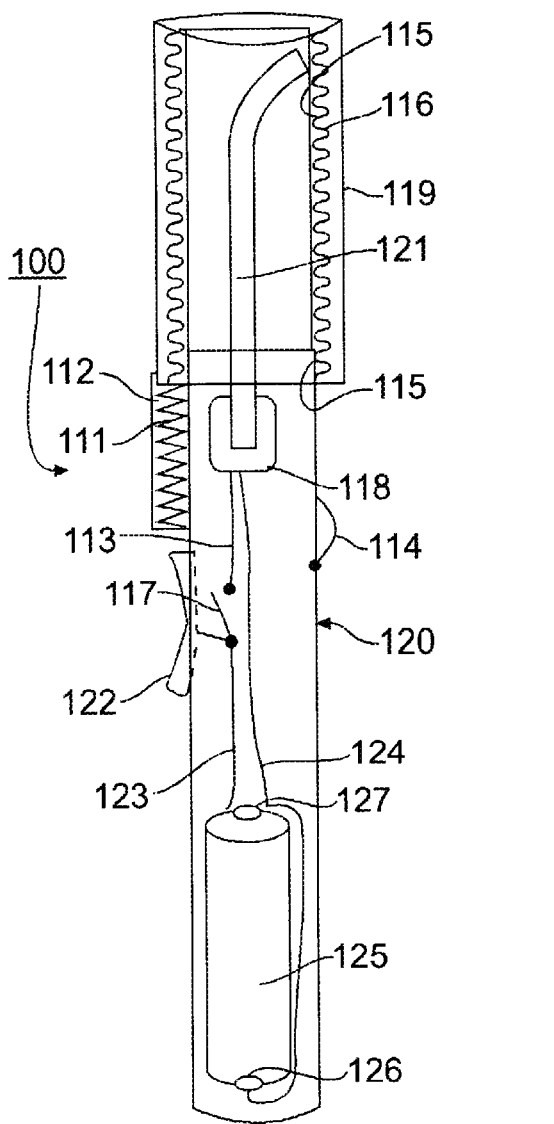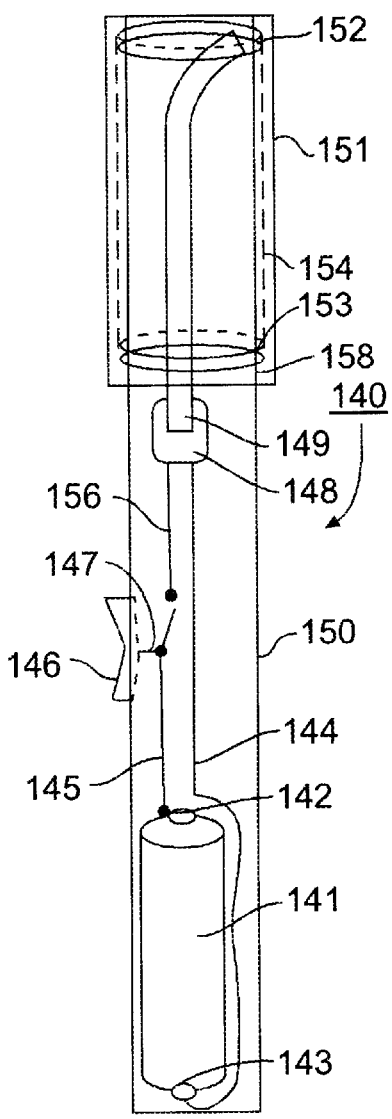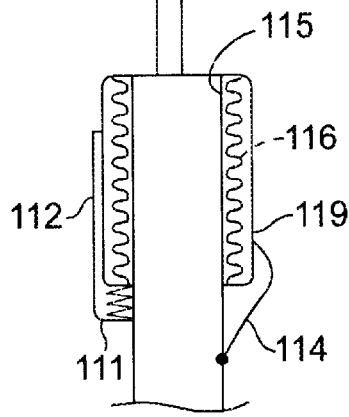
FIG. 3A
FIG. 3B
FIG. 4

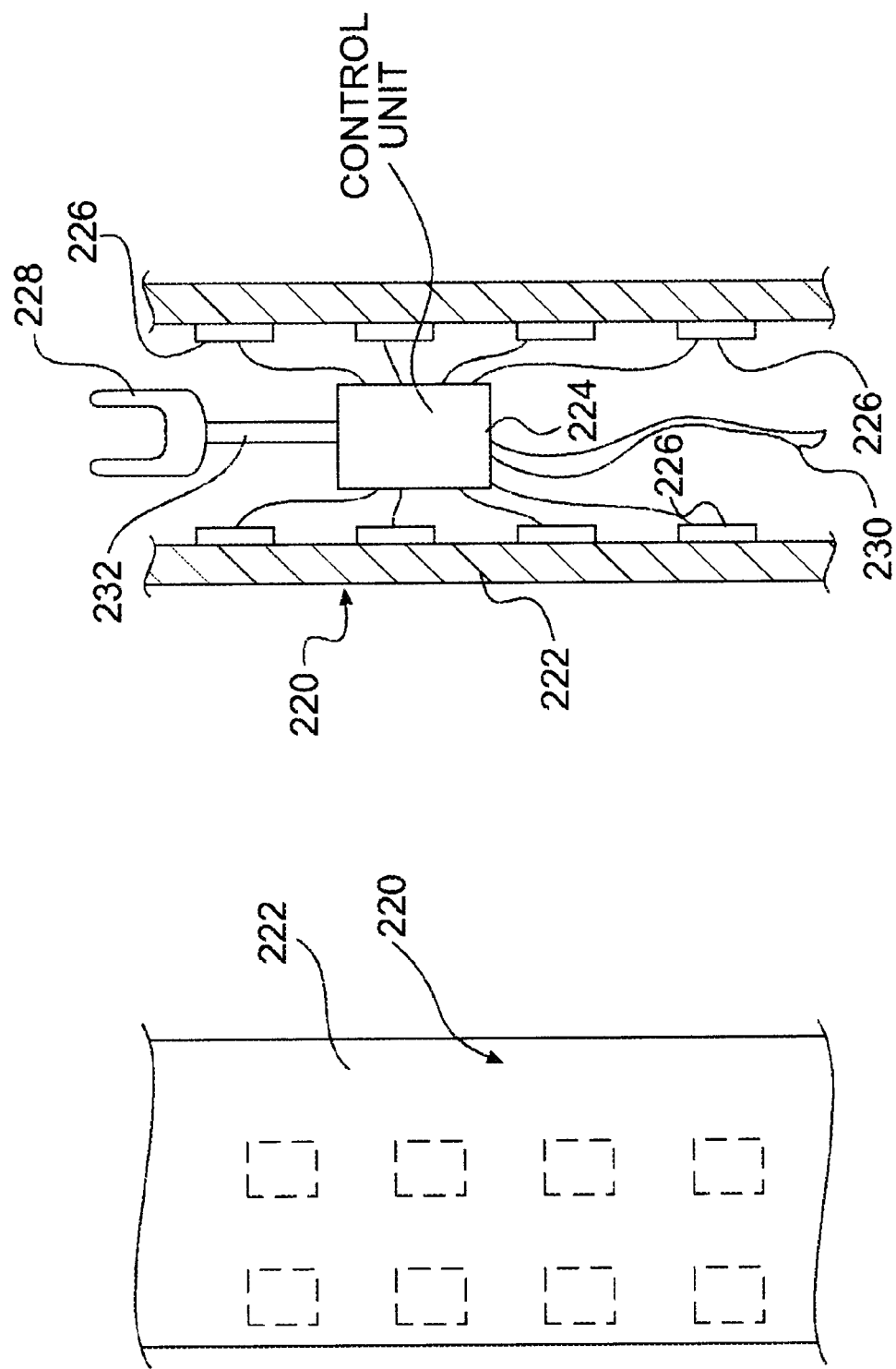

DENTAL INSTRUMENT FOR USE IN ROOT CANAL OBTURATION

CROSS-REFERENCE TO RELATED APPLICATION

This application is a continuation-in-part of U.S. patent application Ser. No. 09/359,252 filed Jul. 22, 1999, now U.S. Pat. No. 6,106,283.

FIELD OF THE INVENTION

The present invention relates to a dental instrument, in particular, an instrument for use in root canal therapy and more particularly in the final stages of root canal therapy during obturation of the root canal systems. In the latter instance, the instrument is capable of thermo-softening gutta percha in the root canal as well as searing off gutta percha in the root canal utilizing a controlled-temperature instrument.

BACKGROUND OF THE INVENTION

At the present time, in root canal therapy, filling material such as gutta percha is inserted into the root canal and deformed, usually by the application of heat and pressure. The gutta percha is then able to flow into many irregularities of the prepared root canal, thus allowing for a three-dimensional obturation and sealing to occur. More specifically, when the gutta percha is softened, it is able to be compressed into the numerous aberrations of the root canal in order to effectively seal the root canal cavity.

The compressing of the gutta percha is performed by using a root canal filling spreader and filling condensors. Some prior art root canal spreader and filling condensers are made of stainless steel or nickel-chromium plated brass. The filling spreaders are smooth, flat-ended and slightly tapered. The conventional means for achieving a heated instrument tip is to heat the tip externally, for example, by holding the tip in a flame or in contact with a resistive heater. One disadvantage of this is that the instrument cools off quite rapidly. Thus, to overcome this and achieve the desired degree of heating at the end of the tip, it is often necessary to heat the tip until it glows. However, this increases the risk of accidental burns and tends to rapidly destroy the tip.

In the obturation of root canal systems during root canal therapy, it is usually necessary to sear off gutta percha, i.e., to apply heat to burn off unwanted filling material (excess gutta percha). This is often accomplished by introducing a dental instrument, such as a so-called plastic instrument, into an existing flame, such as that provided by a Bunsen burner, to heat the same and then applying the heated plastic instrument to the pulp chamber of the tooth having excess gutta percha. In this manner, excessive gutta percha is burned off so that only an amount of gutta percha necessary in the root canal is present. It should be recognized that although gutta percha is a commonly used substance to fill root canals, other deformable or heat moldable material are occasionally used to fill the root canals, but gutta percha will be used hereinafter as synonymous with a filling material for the purposes of this application.

There are several problems with this conventional method. First, the burning flame of the Bunsen burner is a hazard that may ignite other flammable material. Second, the flame must be kept constantly burning during the obturation of the root canal in view of the fact that it is used intermittently during the obturation procedure and it is not cost effective to continually extinguish and relight the flame. Third, the flame is often of such magnitude that it frightens patients (who may not be used to undergoing a dental procedure in the vicinity of a burning flame). Fourth, this obturation method requires frequent transfer of the heated dental instrument between the flame and the patient's mouth. During such transfer(s), it is a continuous hazard that the instrument may inadvertently fall, burning something, more significantly and harmfully burning the mouth of the patient. Further, in view of the necessity of such transfer(s) between the flame and the patient's mouth, there is an obvious loss of heat, i.e., the instrument cools somewhat after it is removed from the flame and before it is used operatively in the patient's mouth. This loss of heat may be significant in view of the fact that the filling material, i.e., the gutta percha, will not melt if the instrument has cooled to a temperature below the melting temperature of the gutta percha.

In the prior art, the general endodontic process for filling a root canal in a tooth with gutta percha is described in U.S. Pat. No. 4,480,996 (Crovatto), U.S. Pat. No. 4,525,147 (Pitz et al.), U.S. Pat. No. 4,681,545 (Lapcevic), U.S. Pat. No. 4,894,011 (Johnson) and U.S. Pat. No. 5,067,900 (McSpadden).

U.S. Pat. No. 4,992,045 (Beisel) describes a self-contained heated root canal dental instrument which combines the operations of a root canal spreader, a root canal condenser and a root canal filling material beater. The instrument includes a frame and a heatable probe mounted to the frame and projecting outward therefrom. Heating means are arranged in connection with the frame for heating the probe. A battery is housed in the frame to provide power to the heating means. A switch is electrically coupled to an interposed between the heating means and the battery.

A similar type of instrument is the Endotec II™ thermal condensor for gutta percha sold by Lone Star Technologies. This instrument is a cordless hand-piece with a quick-change top and enables a dentist to thermo-soften gutta percha in the root canal with a specially designed and shaped, electrically heated instrument tip. The amount of heat is purported to be precisely controllable by the dentist by depressing a heat activator button. Use of this instrument purports to provide the advantage of causing gutta percha to coalesce and fuse into a dense, homogeneous mass. Also, the gutta percha adapts to the shape of the root canal under pressure. A problem with this instrument is the fact that the tip is continuously exposed and uncovered and thus, when heated, can cause damage, e.g., burns to the dentist or patient.

Another inconvenience arises from the fact that the manufacturer suggests inserting the instrument tip into the root canal and then heating the probe by depressing the heat activator button. Although this avoids the problem of having a heated tip exposed before the actual procedure, it causes a delay in the treatment because the tip is only heated after it is inserted into the root canal and not before. Thus, the dentist must wait for the tip to be heated while in the root canal and then perform the necessary application of pressure to soften the gutta percha.

OBJECTS AND SUMMARY OF THE INVENTION

Accordingly, it is an object of the present invention to provide new and improved methods and apparatus for condensing root canal filling material and searing off gutta percha during the obturation phase of root canal therapy.

It is another object of the present invention to provide new and improved methods and apparatus for condensing root canal filling material and searing off gutta percha during the obturation phase of root canal therapy that are safe and effective.

It is yet another object of the present invention to provide new and improved methods and apparatus for condensing root canal filling material and searing off gutta percha during the obturation phase of root canal therapy which substantially avoid the problems with conventional methods and apparatus mentioned above.

It is still another object of the invention to provide a new and improved dental instrument that includes a metal component that is heatable in a safe manner and can be applied in a safe manner to conduct dental treatment in a patient's mouth which requires the application of heat.

It is still another object of the present invention to provide a new and improved dental instrument that avoids the potentially obtrusive presence of a continually burning flame in proximity to the dental patient during dental procedures.

It is yet another object of the present invention to provide a new and improved instrument for condensing root canal filling material and searing off gutta percha during the obturation phase of root canal therapy which enables the instrument tip to be safely heated prior to insertion into a patient's mouth.

It is still another object of the present invention to provide a new and improved dental instrument which includes a heatable tip which is heated while covered upon contact with a human hand, i.e., upon the application of pressure to the instrument.

Briefly, to accomplish at least some of these objectives, one embodiment of an apparatus for use in obturating a root canal in accordance with the invention comprises a first member comprising a frame, a heatable probe mounted to the frame to project outward from the frame and adapted for insertion into or into proximity of the root canal, and at least one pressure sensor for detecting application of external pressure on the first member, each pressure sensor being coupled to the heating probe such that the heating probe is heated upon the application of pressure on the first member. The apparatus also includes a second member for covering the heating probe, the second member being attachable to the first member in a position in which the second member covers the heating probe and movable from the position to expose the heating probe.

The second member may be a retractable cover connected to the first member and having a first position in which the cover covers the heating probe and a second retracted position in which the heating probe is exposed. Displacement means may thus be provided for enabling the cover to move between the first position and the second position. For example, the displacement means may be cooperating threads arranged on an outer periphery of the first member and on an inner surface of the cover. In the alternative, the second member may be a cover slidably connected to the first member such that the cover is slidable between a position in which the cover covers the heating probe and a position in which the heating probe is exposed. This cover may comprise axially extending channels and a respective slot at each end of each channel. The slots extending circumferentially around at least a portion of an inner surface of the cover. The first member includes projections at an upper end, each projection being slidable within a respective channel and slot associated with the channel.

If the first member is a cylindrical tube, the pressure sensor(s) may be arranged on an inner surface of the tube. In the alternative, the pressure sensor(s) may be embedded in a wall of the tube.

Heating means are arranged in connection with the frame for heating the heating probe and power means, e.g., a battery, are arranged in connection with the frame for providing power to the heating means. Control means control the heating means such that heating of the heating probe by the heating means is regulated. The control means are coupled to the pressure sensor(s) and direct the heating means to heat the heating probe when the application of external pressure on the first member is detected by the pressure sensor(s).

Another embodiment of an apparatus for use in obturating root canals comprises a cylindrical housing having an inwardly depressible region, a heatable probe adapted for insertion into or into proximity of the root canal, and a cradle having a seat in which the heating probe is received. The cradle is arranged inward of the depressible region of the housing and constructed such that depression of the region causes displacement of the cradle and movement of the heating probe in an outward direction. Heating means are arranged in the seat of the cradle and in engagement with the heating probe for heating the heating probe.

To activate the heating means, at least one pressure sensor is arranged on the housing for detecting application of external pressure on the housing. The pressure sensor(s) is/are coupled to the heating probe such that the heating probe is heated upon the application of pressure on the housing. Control means are thus also provided for controlling the heating means such that heating of the heating probe by the heating means is regulated. The control means are coupled to the pressure sensor(s) and direct the heating means to heat the heating probe when the application of external pressure on the housing is detected by one or more of the pressure sensors.

Another embodiment of the instrument in accordance with the invention comprises an elongate tube including electrically powered heating means and a curved heating probe coupled to the heating means, and a detachable cover for covering the heating probe of the tube when the heating probe is not in use. The heating means may be either a battery or other electricity storage module housed within the tube or an electric unit having a cord for connection to an external power source. When activated, the heating means function to heat the heating probe that extends at one end of the tube and curves slightly beyond that end of the tube. The cover releasably engages with one end of the tube and is designed to fit over the heating probe but not in contact therewith so that it is possible to heat the heating probe while it is still housed within the cover. The cover defines a space in an interior thereof in which the heating probe is situated and heated by the heating means upon energization thereof. Thus, upon detaching of the cover from its engagement with the tube, the probe has already been heated and is ready for use. On the other hand, after use of the heating probe, it is only necessary to place the cover into engagement with the end of the tube, at which time, the heating means can be turned off if desired. Alternatively, if the heating probe is to be re-used during the course of the dental treatment, the heating means can be maintained in an "on condition".

Thus, one basic embodiment of an apparatus for obturating a root canal comprises a first member comprising a frame, and a heatable probe mounted to the frame to project outward from the frame and adapted for insertion into proximity of the root canal, and a second member for covering the heating probe. The second member is attachable to the first member in a position in which the second member covers the heating probe, and thereby prevents injury resulting from the heated probe, and is also movable from the position to expose the heating probe and enable use thereof. The first member may be a cylindrical tube and the second member a cover adapted to fit over the upper end of the cylindrical tube. To maximize the use of the heating probe for accessing the root canal, the heating probe preferably has a first portion extending parallel to axis of the first member and a second portion adjacent the first portion extending at an angle to the first portion. The thickness of the second portion, including its end, is dimensioned to enable entry into the root canal (the range of sizes of which is known to those skilled in the art) and thus has a very small thickness.

To heat the heating probe, heating means may be arranged in connection with the frame and powered by appropriate power means, either internal such as a battery housed in the frame, or appropriate electrical components to enable connection to a power cord connecting to an outlet. To maintain the temperature of the heating probe at a desired temperature, high enough to enable obturation, control means are provided for controlling the heating means, e.g., a switch electrically coupled to and interposed between the heating means and the power means.

In one embodiment, attachment means are provided for removably attaching the second member to the first member. The attachment means may comprise a first circumferentially extending snap arranged on an exterior surface of the first member and a second cooperating circumferentially extending snap arranged on an interior surface of the second member. Further, the attachment means preferably comprise recesses formed in a lower region of the first snap and projections formed in a lower region of the second snap.

In an enhanced embodiment, securing means are provided for securing the second member to the first member to prevent inadvertent separation of the second member from the first member.

In another embodiment, the second member is a retractable cover connected to the first member and has a first position in which the cover covers the heating probe and a second retracted position in which the heating probe is exposed. Displacement means are provided for enabling the second member to move between the first position and the second position. The displacement means may comprise cooperating threads arranged on an outer periphery of the first member and on an inner surface of the cover. Locking means may also be provided for locking the cover in the second position, e.g., a flexible, metal bracket arranged on an outer peripheral surface of the first member whereby one end of the bracket is attached to the outer surface of the first member and an opposite end of the bracket is free and displaceable by flexure toward and away from the outer surface such that at least a portion of the cover is insertable between the free end of the bracket and the outer surface of the first member. Biasing means such as a spring may also be provided for maintaining the cover in the first position.

In yet another embodiment, the second member is a cover slidably connected to the first member. The cover comprises axially extending channels and a respective slot at each end of each channel. The slots extend circumferentially around at least a portion of an inner surface of the cover. The first member includes projections at an upper end, each projection being slidable within a respective channel and slots associated therewith.

Another embodiment of the apparatus for obturating a root canal, comprises housing means defining an interior compartment, e.g., a tubular structure, a displaceable unit comprising a heatable probe adapted for insertion into proximity of the root canal, and heating means for heating the probe, and displacement means for moving the unit from a first position in which the probe is in the compartment to a second position in which the probe is outside of the compartment. The unit can include a frame on which the heating means and the probe are mounted and a battery coupled to the heating means for supplying power to the heating means. The displacement means may comprise an appendage attached to the unit and extending outside of the compartment, e.g., a circular disc and a shaft extending from the disc to the unit. Cooperating securing means are preferably arranged on the housing means and the unit for securing the unit in the first position in which the probe is exterior of the compartment and the second position in which the probe is inside the compartment.

Another similar embodiment of the instrument includes a pushbutton connected to the unit while the housing means including a slot having a pair of circular regions adapted to receive a spherical part of the pushbutton. The pushbutton further includes a rigid component connected to the unit and a spring interposed between the rigid component and the pushbutton.

BRIEF DESCRIPTION OF THE DRAWINGS

The invention will be described with reference to the accompanying non-limiting drawings wherein:

FIG. 3A is a cross-sectional view of another embodiment of the instrument in accordance with the invention;

FIG. 3B is a view of the embodiment of the instrument in accordance with the invention shown in FIG. 3 with the cover in its retracted position;

FIG. 4 is a cross-sectional view of yet another embodiment of the instrument in accordance with the invention;

FIG. 7 is a front view of another embodiment of the instrument in accordance with the invention;

FIG. 7A is a partially schematic, interior view of the instrument shown in FIG. 7;

DETAILED DESCRIPTION OF THE PREFERRED EMBODIMENTS

Figure 1:
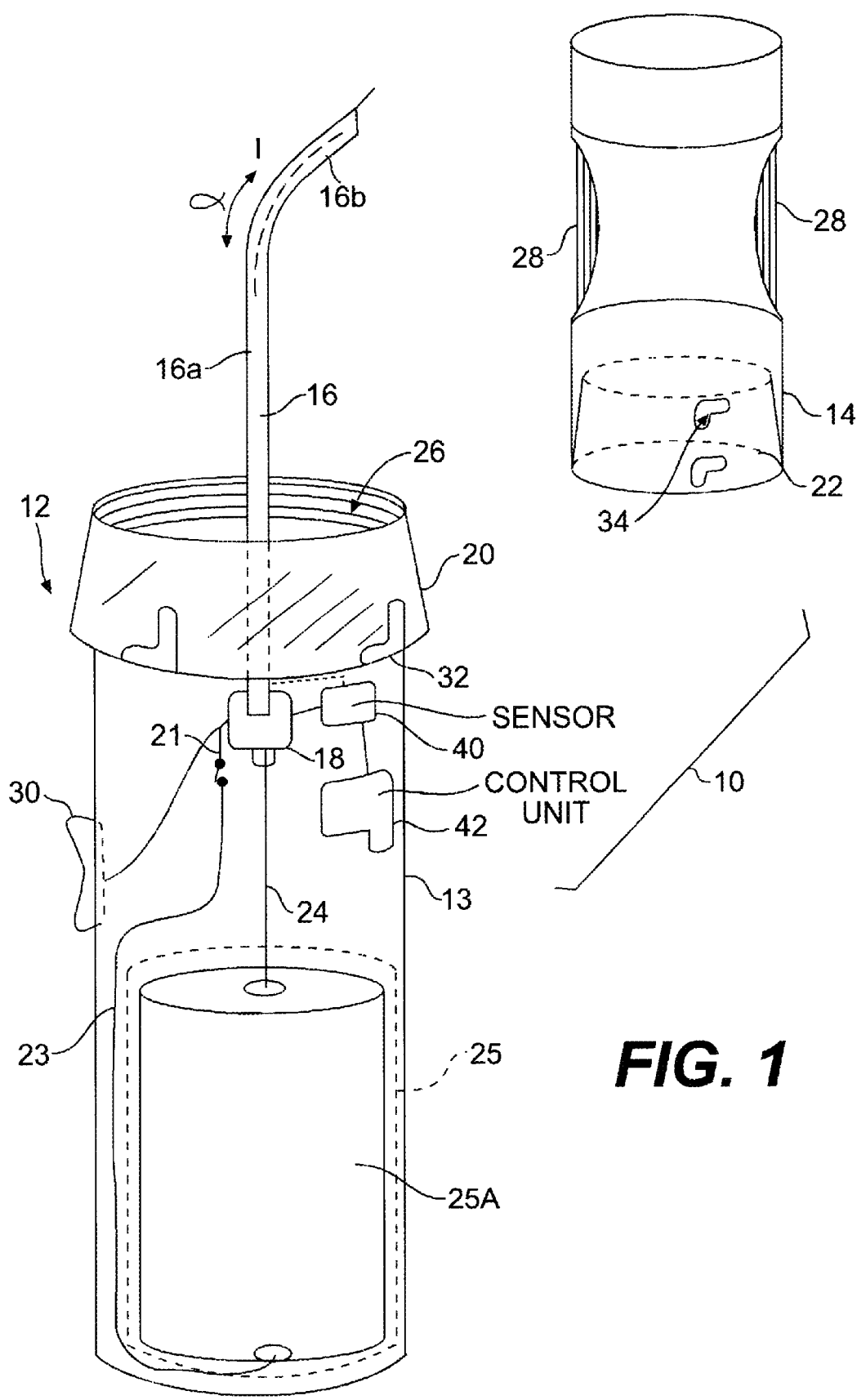
FIG. 1 is a perspective view of the apparatus in accordance with the invention in which the cover member is separate from the base member.

Referring to the accompanying drawings wherein like reference numerals refer to the same or similar elements, the apparatus in accordance with the invention is denoted generally at 10 and comprises two members, an elongate substantially cylindrical member 12 and a cover member 14 adapted to mate with the cylindrical member or tube 12. Generally, the cylindrical member 12 includes a frame 13, a heatable probe 16 mounted on the frame 13 in an outwardly extending position from one end 26 of the frame 13 and heating means 18 for heating the probe 16. The probe 16 is made of any suitable heatable material such as a metal, and is ideally provided with a curvature at an end distal from the frame 13 as shown in FIG. 1. The heating means 18 may comprise a conventional heating unit that may be thermally coupled to the heating probe 16 so that heat generated by the heating unit is transferred to the heating probe 16. In the alternative, the heating means 18 may be a simple seat made of an electrically conductive material or any other appropriate means for heating the probe 16 upon completion of an electrical circuit therewith.

The frame 13 houses power means for providing power to the heating means 18, such as a battery 25A received in a battery compartment 25 defined in frame 13. When activated to supply power to the heating unit 18, battery 25A provides electrical power through electrical coupling means such as wires 23,24 extending between the terminals of the battery 25A and the heating means 18. The frame 13 may also comprise appropriate thermal insulation to prevent the outer surfaces of the cylindrical member 12 from becoming hot. The connections of the wires 23,24 to the terminals of the battery 25A are common knowledge and within the skill of one versed in the art.

To provide for selective heating of the probe 16 by the heating means 18, i.e., heating of the probe 16 when desired, an electrical switch 21 is situated in connection with the wire from one of the terminals of the battery 25A to the heating means 18. When the switch 21 is closed, an electrical circuit is completed between the terminals of the battery 25A and the heating means 18 through wires 23,24 so that the heating means 18 are enabled to heat the probe 16. However, when the switch 21 is open, the electrical circuit is not completed and the heating means 18 are not operable to heat the probe 16. The activation of the switch 21 is caused by the placement of a switch 30 on an outer wall of the frame 13 whereby the switch 30 is positionable in at least two different positions, one in which switch 21 is closed and the other in which switch 21 is open. Depressing switch 30 will therefore enable heating of probe 16 while release of the switch 30 will cease heating of the probe 16.

The construction of switches 21,30 may be any conventional manually activated electrical switches designed to enable manual control of the heating means 18. For example, the control means of the heating means 18 may be constituted by a control on the battery 25A which toggles the power output of the battery 25A so that when the battery 25A supplies power, the heating means 18 are operable and when the power is toggled, power is not supplied to the heating means 18.

In the alternative, as shown in FIG. 1, a temperature sensor 40 is placed in conjunction with the heating means 18 (or probe 16 shown in dotted lines) in order to measure the temperature of the probe 16. As such, a control unit 42 is arranged in association with frame 13, and coupled to temperature sensor 40, in order to receive the measured temperature of the probe 16 from the temperature sensor 40 and activate the heating means 18 in order to provide for a desired temperature of the probe 16. The temperature of the probe 16 may thus be maintained in a defined range of temperature whereby if the temperature of the probe 16 falls outside of the range, the control unit 42 functions to cause the heating means 18 to heat the probe 16 until the temperature of the probe 16 is either within the range or just beyond the range. At this point, the control unit 42 would direct the heating means 18 to cease operation. The exact temperature to which the probe 16 is heated would depend on several factors, bearing in mind that the tip of the heating probe should preferably be red hot. Thus, the factors include the material of the probe 16, or at least the material of the tip of the probe 16 if the probe is made of different materials. In this regard, the probe can be made of different materials, the arrangement of which is designed to maximize the heat transmission to the tip. Other control schemes could also be employed by the control unit 42, e.g., a timed operation whereby the control unit activates the heating means 18 for a set period of time at periodic intervals.

To restrict the exposure of the heating probe 16 only to the times when it is required for the root canal treatment, attachment means are provided for detachably/releasably coupling the cover 14 to the end 26 of the member 12 from which the heating probe 16 projects. Specifically, a cooperating snap 20 is arranged on an exterior surface of the member 12 proximate the end 26 of the member 12 and a cooperating snap 22 is arranged on an interior surface of the cover 14. The snaps 20,22 extending circumferentially around the corresponding surface. To provide a secure attachment, L-shaped recesses 32 are formed in a lower region of the snap 20 and projections 34 are formed in the lower region of the snap 22. For attachment, the projections 34 are received in a respective one of the recesses 32 and the cover 14 is turned such that the projections 34 are grasped by edges of the recesses 32 and retained therein. Other appropriate attachment means and securing means are of course possible to use in the invention without deviating from the scope of the invention. The cover 14 enables the heating probe 16 to be heated while it is still housed within the cover 14 thereby avoiding several problems endemic in the prior art root canal treatment, viz., having an exposed flame which may frighten patients and the necessity to transfer an instrument from a heating source a relatively long distance into the patient's mouth.

Figure 2:
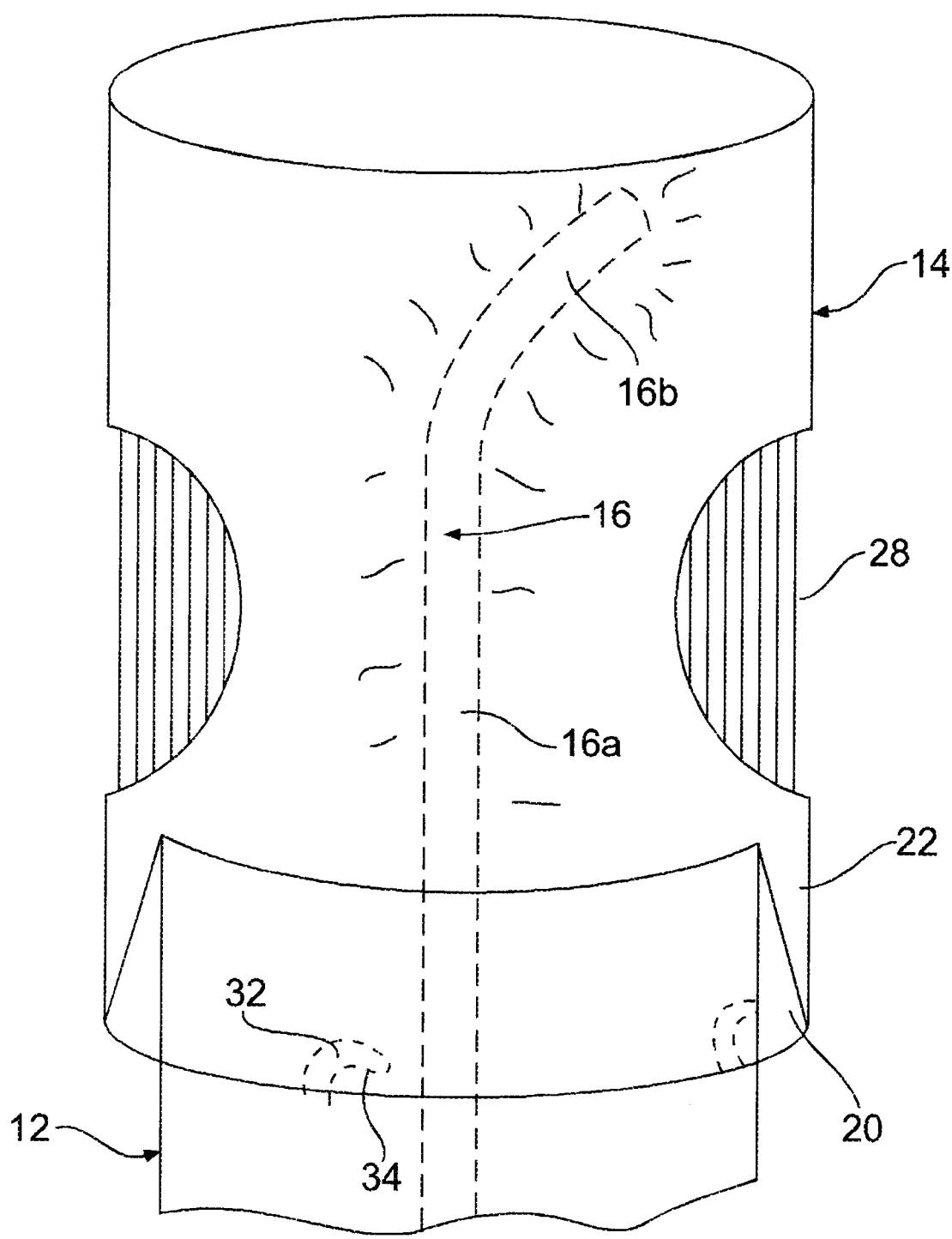
FIG. 2 is a partial view of the apparatus in accordance with the invention in which the cover member is in engagement with the base member and the heating probe is being heated.

The cover 14 is "over-sized", i.e., has a size so that it fits over the heating probe 16 without contacting the same (se FIG. 2). Further, cover 14 includes thumb grips 28, i.e., parallel ridges or indentations, to aid in removal of the cover 14 from its position in engagement with member 12. Alternative thumb grips such as roughenings may also be provided on the outer surface of the cover 14.

As noted above, switch 30 controls the opening and closing of the switch 21 thereby controlling the operation of the heating means 18 for activating the same to heat the heating probe 16, when desired. When not in use, the switch 30 is in its off position so that switch 21 is open and the heating probe 16 is not heated and may cool. The switch 30 may be provided with a locking mechanism (not shown) to lock the switch 30 in the on position and/or the off position. If the switch 30 is lockable in the off position, then it will be necessary to maintain pressure on the switch 30 during use of the heated probe 16. On the other hand, if the switch 30 is lockable in the on position, then it will be possible to use the heated probe 16 without concern as to continually applying pressure on the switch 30, which may be advantageous in certain situations, i.e., expected extended use.

Instead of the battery 25A, alternative electrical power means may be used. These may include an electrical unit housed within the member 12 and a cord for connecting the electrical unit to external electrical sources. In this instance, the size of the instrument can be made quite small in view of the absence of the battery and the continual miniaturization of electrical components.

In the illustrated embodiments, the heating probe 16 has a straight portion 16a adjacent to the end 26 of the member 12 and another straight portion 16b arranged at an angle a with respect to the portion 16a. By providing the heating probe 16 with such an angle, it is easier to access the gutta percha in the root canal which must be seared off at the end of the root canal treatment. Although such an angle is preferred, it is nevertheless possible to construct the heating probe 16 to be entirely straight and oriented either parallel or even coincident with the axis of the member 12 or at an angle to the axis of the member 12.

It should be understood by those skilled in the art that the manner in which the heating probe 16 is heated is not limited solely to the use of a battery 25A and an electrical heating means 18 electrically coupled thereto and both of which are housed within an interior of the member 12. Rather, it is within the scope of the invention that any conventional and/or suitable heating means, battery-powered or powered by an external electrical source or located entirely exterior of the tube, can be used to provide heat energy to the heating probe. Preferably, as noted above, the application of heat to the heating probe 16 will be controlled by appropriate heat regulation means to prevent the heating probe from being heated to an excessive temperature or to a temperature below the required temperature to melt or burn away the excessive gutta percha in the root canal being operated on in the patient's mouth.

In one possible embodiment, it is foreseen that the heating probe 16 can be heated by microwave radiation applied from a microwave source, the remaining portions of the apparatus being constructed to be microwave-durable to prevent damage from exposure in the microwave field and/or being shielded during irradiation of the apparatus. Of course, the heating probe 16 should be constructed from a material which will be heated during exposure to a microwave field, which type of material can be readily ascertained.

It is also recognized that although gutta percha is the most common material used to fill a root canal and upon which the instrument in accordance with the invention will be applicable, the invention is equally applicable on other root canal filling materials that are spread and condensed in the root canal and which require heat in order to eliminate excess material.

In the embodiment shown in FIGS. 3A and 3B, the instrument in accordance with the invention is designated generally as 100 and comprises a narrow cylindrical member tube 120 having a compartment for receiving and retaining a battery 125 such as an AA or AAA size having a positive terminal 127 and a negative terminal 126. A wire 124 is electrically coupled at one end to the negative terminal 126 of the battery 125 and electrically coupled at a second end to heating unit 118. A second wire 123 is electrically coupled at a first end to the positive terminal 127 of the battery 125 and connects to a switch 117. Switch 117 is controlled by an on-off knob or switch 122 such that when the knob 122 is in its on position, the switch 117 is closed and engages a third wire 113 electrically coupled to the heating unit 118. In this manner, a complete electrical circuit is formed including the heating unit 118 and the battery 125. A heating probe 121 is coupled to the heating unit 118 and is heated upon activation of the heating unit 118 by the battery 125.

In this embodiment, instead of the removable cover 14 as shown in FIGS. 1 and 2, a retractable cover 119 is coupled to the tube 120. This embodiment thus has the advantage that the cover is never completely separated from the tube 120 and cannot be lost or misplaced. Again, as in the embodiment of FIGS. 1 and 2, it is possible to heat the probe 16 while it is still housed within the cover 119. However, in this embodiment, instead of removing the cover to use the probe, it is simply possible to twist the cover 119 with respect to the tube 120 thereby causing the cover 119 to move downward along an outer periphery of the tube 120 toward the battery 125 (in the illustrated embodiment). The twisting of the cover 119 with respect to the tube 120 is facilitated by the presence of cooperating threads 115,116 on the inner surface of the cover 119 and an uppermost portion of the outer peripheral surface of the tube 120. For the sake of simplicity and easy access, it is preferable to provide only a minimum number of threads.

In this embodiment, it is necessary to ensure that the cover 119 remains in its position whether it is the probe-exposing position as shown in FIG. 3B or the probe-concealing position as shown in FIG. 3A. To this end, the instrument 100 includes locking means for locking the cover 119 in the probe-exposing position. These locking means comprise a flexible, metal bracket 114 arranged on an outer peripheral surface of the tube 120. One end of the bracket 114 is attached to the outer surface of the tube 120 and the other end of the bracket 114 is free and displaceable by flexure toward and away from the outer surface. In this manner, upon the descent of the cover 119, at least a portion of the cover 119 is insertable between the free end of the bracket 114 and is retained securely in the probe-exposing position thereby. Other locking means, such as a snap-fit connection, latch, belt, tongue and groove arrangement as well as any other releasable attachment means such as hook and loop fasteners (e.g., VELCRO™), may be used in the invention without deviating from the scope of the invention.

To maintain the cover 119 in its probe-concealing position as shown in FIG. 3A, the instrument 100 includes biasing means such as a spring 111 contained in a housing 112. One end of the spring 111 is exposed through an opening in the housing 112 and engages the lower surface of the cover 119.

In the embodiment shown in FIG. 4, the instrument in accordance with the invention is designated generally as 140 and comprises a narrow cylindrical member or tube 150 having a compartment for receiving and retaining a battery 141 such as an AA or AAA size having a positive terminal 142 and a negative terminal 143. A wire 144 is electrically coupled at one end to the negative terminal 143 of the battery 141 and electrically coupled at a second end to heating unit 148. A second wire 145 is electrically coupled at a first end to the positive terminal 142 of the battery 141 and connects to a switch 147. Switch 147 is controlled by an on-off knob or switch 146 such that when the knob 146 is in its on position, the switch 147 is closed and engages a third wire 156 electrically coupled to the heating unit 148. In this manner, a complete electrical circuit is formed including the heating unit 148 and the battery 141. A heating probe 149 is coupled to the heating unit 148 and is heated upon activation of the heating unit 148 by the battery 141.

In this embodiment, instead of the removable cover 14 as shown in FIGS. 1 and 2 and the a retractable cover 119 shown in FIGS. 3A and 3B, a sliding cover 151 is provided. Cover 151 includes a plurality of axially extending channels 154 formed in an inner circumferential surface and a respective slot 152,153 at the ends of each channel 154. Slots 152,153 extend circumferentially around at least a portion of the inner surface of the cover 151. The tube 150 includes projections 158 at an upper end, each slidable within a respective channel 154 and the associated slots 152,153. The number of projections 158 corresponds to the number of channels 154. This embodiment thus has the advantage that the cover 151 is never completely separated from the tube 150 and cannot be lost or misplaced. As in the embodiments described above, it is possible to heat the probe 149 while it is still housed within the cover 151.

In this embodiment, in a storage and optional heating state, each projection 158 is situated in a respective lower slot 153. To use the probe 149, the cover 151 is twisted with respect to the tube 150 thereby causing the projections 158 to slide within the slots 153 until they align with a respective channel 154. The cover 151 is drawn downward toward the tube 150 along an outer periphery of the tube 150 until the projections 158 align each with a respective upper slot 152. The cover 151 is then twisted to cause the projections 158 to enter into the slots 152 and thereby retain the cover 151 is a position in which the probe 149 is exposed and available for use.

In this embodiment, it would be desirable to ensure that the cover 151 remains in its position whether it is the probe-exposing position or the probe-concealing position. To this end, the cover 151 or the tube 150 could include locking means for locking the cover 151 in its position. For example, such locking means might be provided by spring-biasing the projections 158 and providing a deeper recess at an end of each slot 152,153. The spring would bias the projections outward into these slots and prevent inadvertent displacement of the cover 151 during operation.

In the embodiment shown in FIGS. 5A and 5B, the instrument in accordance with the invention is designated generally as 170 and comprises a narrow cylindrical member or tube 172 having a displaceable unit or sled 174. Displacement unit 174 includes a frame 176 on which a battery 175 is mounted, heating means 178 and a probe 180 are stationarily arranged for movement with the frame 174. The frame 174 also includes protrusions 182 extending radially outward and a manually accessible appendage 184. Tube 172 includes a switch 186 on an exterior surface controlling an electrical switch 188 which when closed provides electrical current from the battery 175 to the heating means 178 (see FIG. 5B). Tube 172 also includes projections 190 on an interior surface for cooperating with the protrusions 182 on the frame 176.

In its storage position shown in FIG. 5A, the probe 180 is situated in the interior chamber 192 defined in the tube 172. Upon depressing switch 186, the electrical switch 188 is closed thereby energizing the heating means 178 and causing the probe 180 to heat up. (Heating of the probe 180 may occur while the probe is in the compartment 192 and/or when the probe 180 is outside of the compartment 192 as shown in FIG. 5B.) When the probe is needed for the root canal procedure, the dentist depresses appendage 184 causing release of the protrusions 182 from between the lower set of projections 190 and allowing the unit 174 to slide (upward) within the tube 172 until the protrusions 182 are secured between the upper set of projections 190. To this end, the projections 190 and protrusions 182 may be appropriately constructed in several known ways to allow for release of the unit 174 from a fixed position relative to the tube 172 only upon manual activation of the appendage 184. This will prevent inadvertent and unwanted movement of the unit 174, and thus the probe 180. Once the protrusions 182 are secured between the upper set of projections 190, the probe 180 is exterior of the tube 172 and ready for use. When the procedure is finished, the dentist pulls the appendage to release the protrusions 182 from the upper set of projections 190 and continues pulling until the protrusions 182 are situated between the lower set of projections 190.

It is also possible to construct the protrusions 182 and projections 190 to require twisting (rotation) of the appendage 184 to enable release of the protrusions 182 from the projections 190. Also, guide means for guiding the sliding movement of the unit 174 in the tube 172 should be provided.

Figure 5:
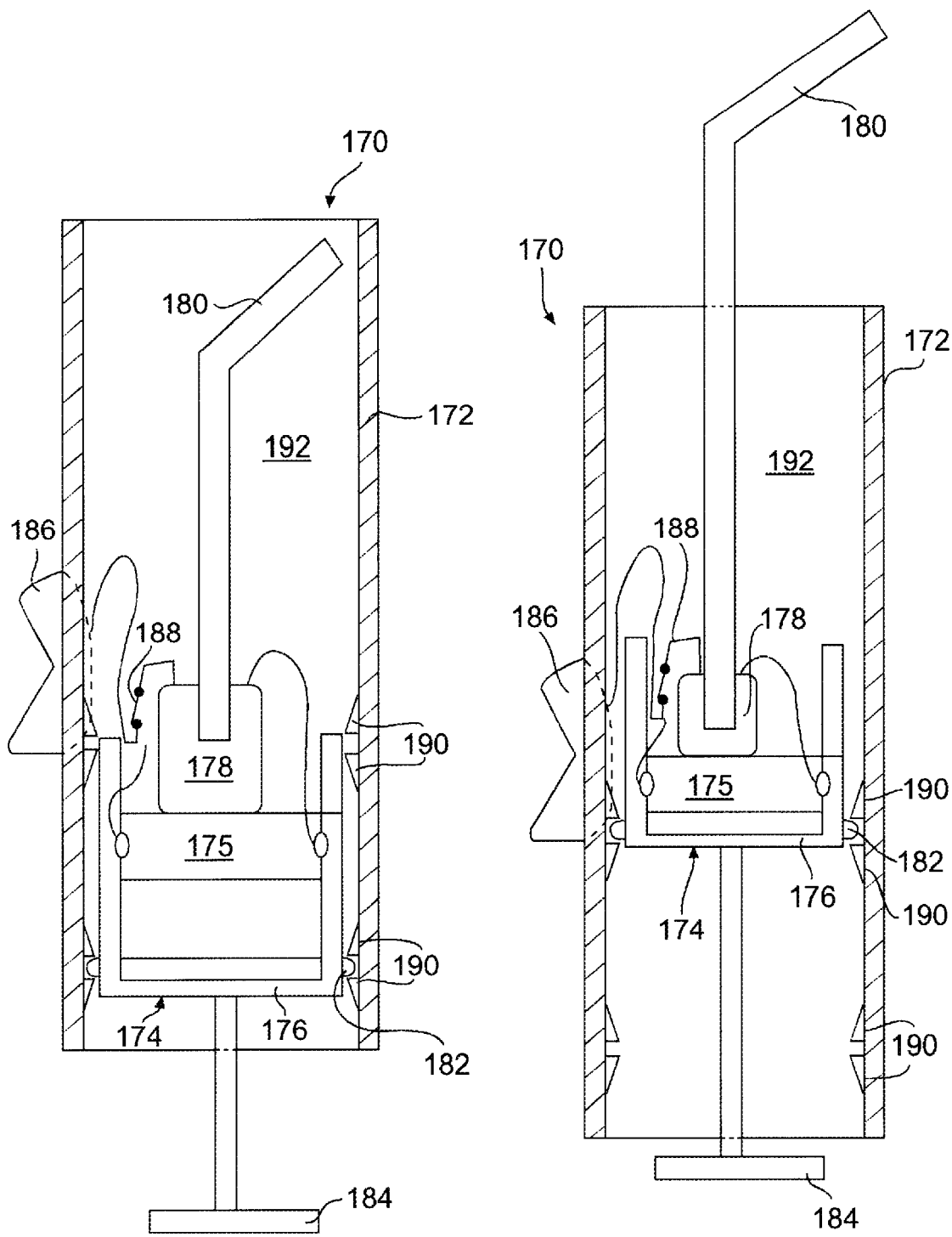
FIG. 5A is a cross-sectional view of another embodiment of the instrument in accordance with the invention in which the heating probe is housed in the instrument.
FIG. 5B is a cross-sectional view of the embodiment shown in FIG. 5A wherein the heating probe is exposed and available for use.
Figure 6:
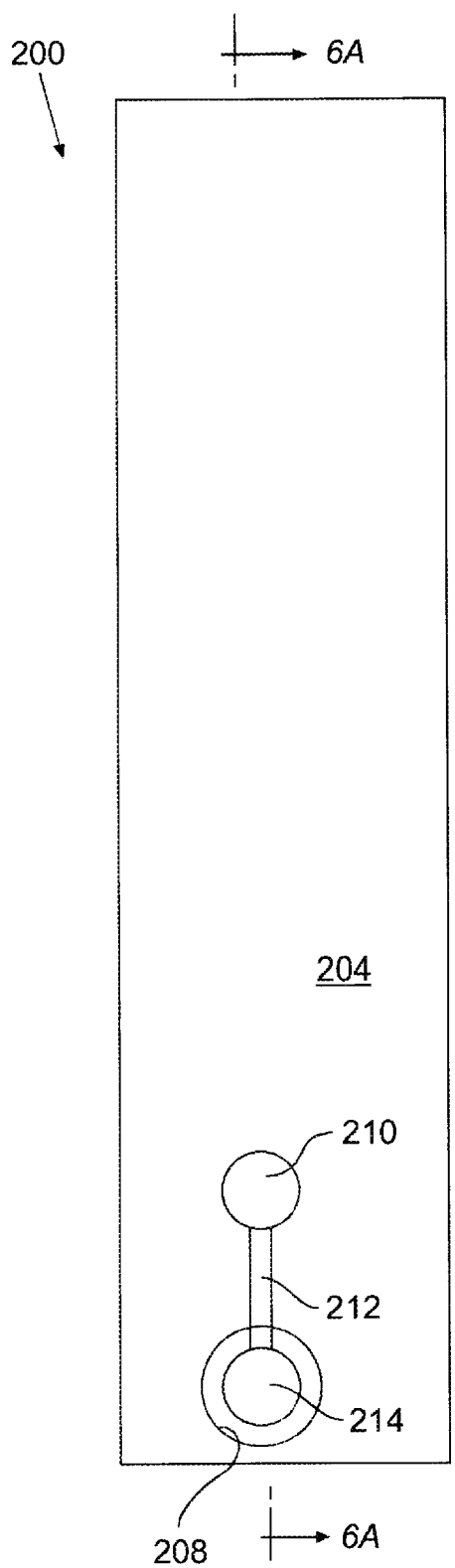
FIG. 6 is a front view of another embodiment of the instrument in accordance with the invention.
Figure 6A:
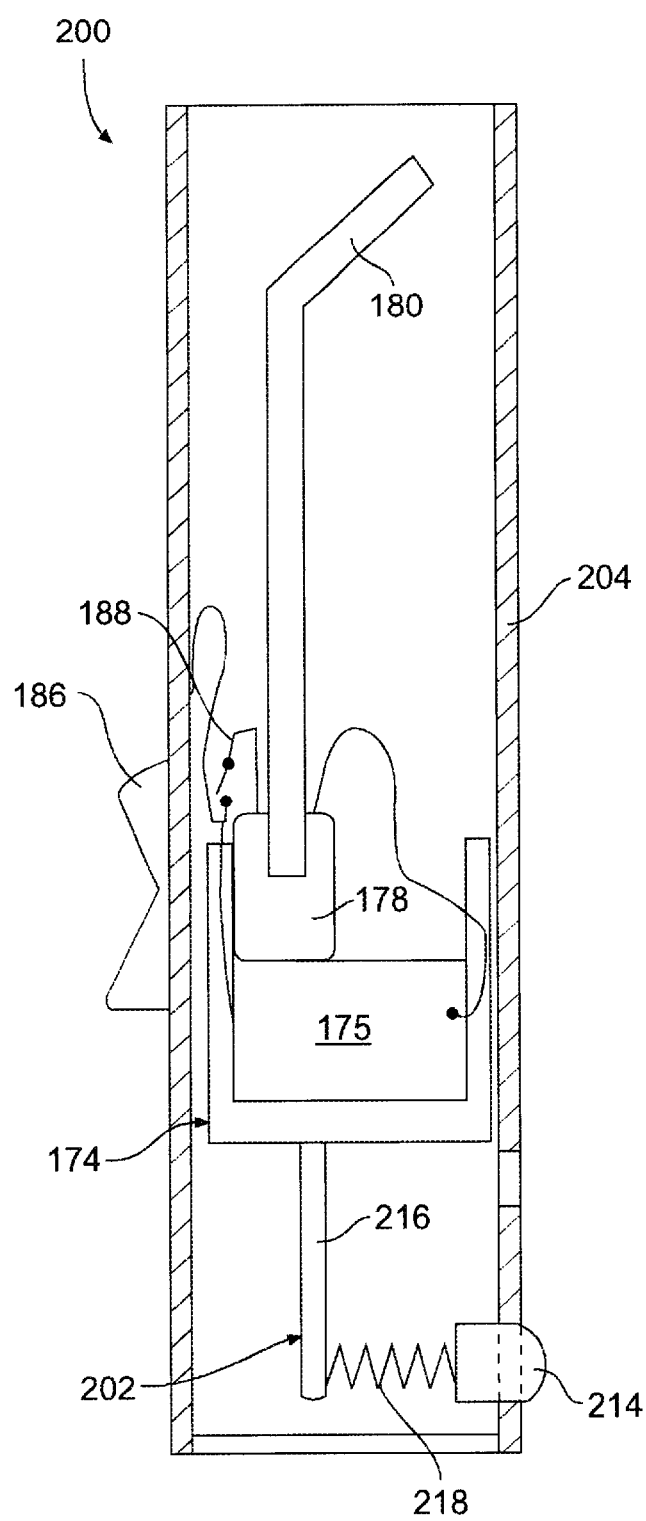
FIG. 6A is a cross-sectional view of the instrument shown in FIG. 6 taken along the line 6A—6A of FIG. 6.
Figure 8:
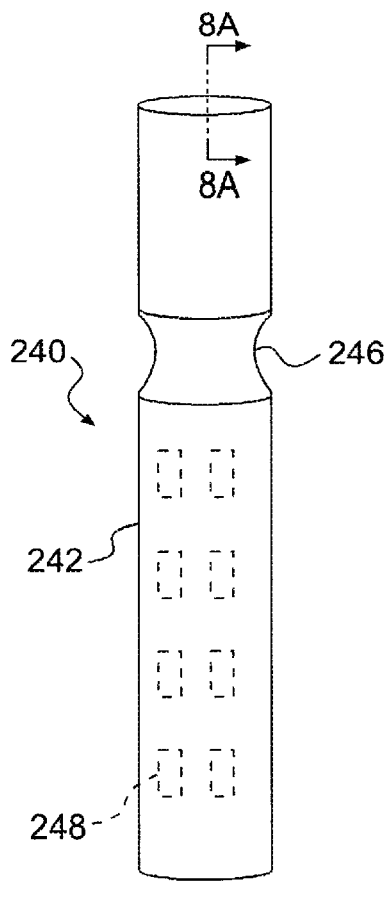
FIG. 8 is a front view of another embodiment of the instrument in accordance with the invention.
Figure 8A:
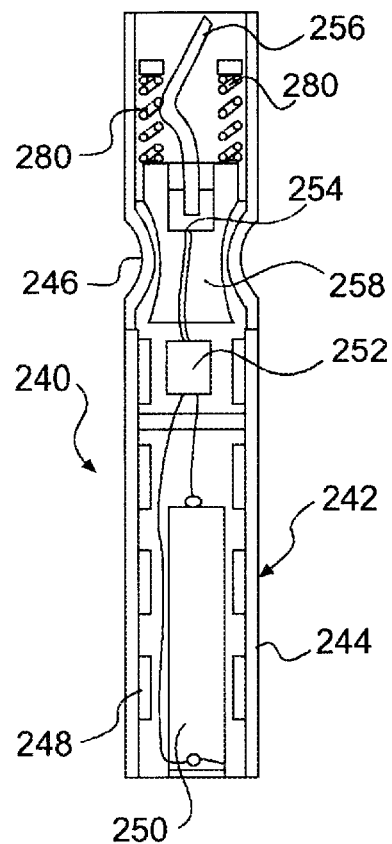
FIG. 8A is cross-sectional view of the instrument shown in FIG. 8 taken along the line 8A—8A of FIG. 8.

In another embodiment shown in FIGS. 6 and 6A, which is similar in most respects to the embodiment shown in FIGS. 5A and 5B and thus the same reference numerals are used to designate the same elements, instead of appendage 184, the instrument (designated 200) includes a pushbutton 202 and the tube 204 includes an elongate slot 206 having circular regions 208,210 and a straight portion 212 therebetween. The pushbutton 202 includes a spherical part 214 adapted to pass at least partially through the circular regions 208,210 a rigid component 216 connected to the unit 174 and a spring 218 coupling the spherical part 214 to the component 216.

In its storage position shown in FIG. 6A, the spherical part 214 of the pushbutton 202 is in the lower circular region 208. Upon depressing switch 186, the electrical switch 188 is closed thereby energizing the heating means 178 and causing the probe 180 to heat up although heating of the probe 180 may occur while the probe is in the compartment 192 and/or when the probe 180 is outside of the compartment 192. The dentist then presses spherical part 214 inward against the bias of spring 218 and then upward so that the spherical part 214 slides in the straight portion 212 into the upper circular region 210. The dentist releases the inward pressure on spherical part 214 so tat the spherical part 214 is urged outward upon expansion of spring 218 into the circular region 210. Movement of the pushbutton translates into movement of the unit 174 and thus inward and outward movement of the probe 180.

In the embodiments of FIGS. 5–6A, instead of providing unit 174 on which the battery 175, heating means 178 and probe 180 are mounted, it is possible to mount the battery 175 in a fixed position in the tube 172 such that only the heating means 178 and probe 180 are movable. The wires connecting the battery 175 to the heating means would be dimensioned to allow for movement of the heating means 178 relative to the battery 175. Also, as noted above, the battery could be replaced by appropriate electrical components to allow for an external power source, i.e., connections for a plug.

The probe and heating means used in the invention may be a dental tool of the type shown in U.S. Pat. No. 4,992,045. This dental tool comprises a cannula or hollow tapered tubing, a conductor contained within the tapered tubing which provides an electrically conductive path from the cylindrical handle member to a resistive element in the working tip of the tapered tubing. The conductor and resistive element together represent the core wire. An insulator separates and electrically insulates the conductor from the tapered tubing. In use, when a circuit is completed from the battery, electric current travels through the conductor to the resistive element in the tip which thereby generates the heat required for the use of the dental tool in condensing gutta percha or searing off gutta percha. Thus, the heating means could be integrated with the probe. Furthermore, although a switch provides only for opening and closing the electrical circuit in this type of dental tool, those skilled in the art will recognize that a variable resistor may be provided in series with the switch which may be used to control the heating of the probe by reducing the total current that reaches the resistive element.

FIGS. 7 and 7A show another embodiment of the invention wherein the switch for activating the heating means as the embodiments described above is replaced by one or more pressure sensors arranged in a cylindrical sleeve. The cylindrical sleeve 220 can therefore serve as a replacement for a portion of the frame 13 and switch 30 of the embodiment in FIGS. 1 and 2, a portion of the tube 120 and switch 122 of the embodiment in FIGS. 3A and 3B, a portion of the tube 150 and switch 146 of the embodiment of FIG. 4, a portion of the tube 172 and switch 176 of the embodiment of FIGS. 5A and 5B and a portion of the tube 204 and switch 186 of the embodiment in FIGS. 6 and 6A.

Sleeve 220 includes a circular wall 222 and pressure sensors 226 arranged along an inner surface of the wall 222. The pressure sensors 226 are coupled to a control unit 224 which in turn is coupled to the heating means 228 via cable 232 and to a battery (not shown) via cable 230. The heating means 228 heat the probe in the manner discussed in any of the embodiments above with the control unit 224 selectively activating the heating means. The pressure sensors 226 are designed to detect the application of pressure on the wall 222, which can result from the grasping of the instrument by the practitioner and squeezing the sleeve 220. A signal indicative of the application of pressure, or in more enhanced embodiments, a signal indicative of the magnitude of the pressure exerted on the sleeve 220, is generated by each pressure sensor 226 and directed to the control unit 224. The control unit 224 receives the signal(s) indicative of the application of pressure and controls the heating means 228 to heat the probe (not shown), i.e., it allows for the transfer of electricity from the battery through cables 230 to the heating means 224.

If the magnitude of the pressure is detected by the pressure sensors 226 and directed to the control unit 224, the control unit 224 can control the heating means 228 to heat the probe to a set temperature based on the magnitude of the pressure. Thus, the harder the practitioner presses on the sleeve 220, the hotter the probe will be while a lighter application of pressure will result in a less hot probe.

The control unit 224 could be eliminated from this embodiment and the function thereof incorporated into the heating means 228 or the pressure sensors 226. In the former case, the signals indicative of the application of pressure and/or magnitude of pressure are directed directly to the heating means 228. The heating means 228 may thus be designed to heat the probe based on the signals received directly from the pressure sensors 226 and/or heat the probe to a set temperature based on the magnitude of the pressure applied to the sleeve.

The pressure sensors 226 may be incorporated into the wall 222 of the sleeve, i.e., to possibly enhance the detection of the application of pressure on the sleeve 220.

Also, the number of pressure sensors can be as desired. Indeed, a single pressure sensor may be used but in this case, the location of the pressure sensor should be clearly demarcated on the sleeve 220. Release of the application of pressure on the wall 222 will be detected by pressure sensors 226 which in turn will direct a signal indicative of the absence of pressure to the control unit 224 which will cease the flow of electricity to the heating means 228.

The control unit 224, when present, may be mounted on the wall 222 of the sleeve 220. When the sleeve 220 is incorporated into the embodiment of FIGS. 5–6A, the control unit may be mounted on the frame 174. The actual construction of the control unit to allow electrical flow from the battery to the heating means upon the receipt of specific signals from the pressure sensors, and possibly signals from the control unit to the heating means as for heating the probe to a set temperature based on the magnitude of the pressure, is within the ability of one of ordinary skill in the electrical art based on the disclosure herein and it is believed that it can be realized without undue experimentation.

FIGS. 8–12 show another embodiment of the dental instrument in accordance with the invention. In this embodiment, the instrument designated 240 includes a cylindrical housing 242 having a cylindrical wall 244 and pressure sensors 246 on an inner surface thereof or embedded therein. Cylindrical wall 244 includes a depressed region 248, the function of which is discussed below. The instrument 240 also includes a battery 250, a control unit 252 electrically coupled to the battery 250 and the pressure sensors 246, heating means 254 for heating a probe 256 and a cradle 258 on which the heating means 254 are mounted.

The control unit 252, heating means 254 and pressure sensors 246 cooperatively function as described above with respect to FIGS. 7 and 7A.

Figure 9:
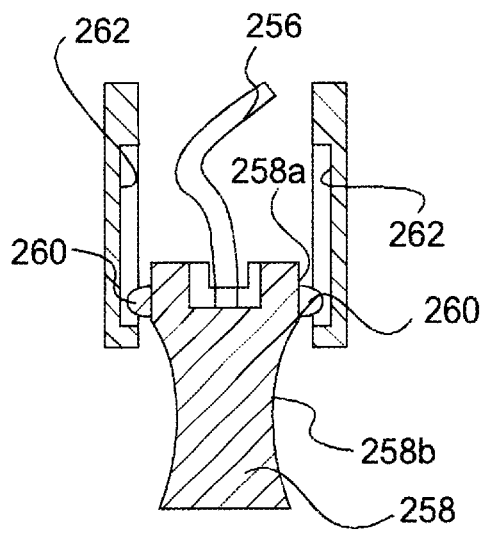
FIG. 9 is a cross-sectional view of the cradle of the instrument shown in FIG. 8.

As shown most clearly in FIG. 9, the cradle 258 has a wide upper region 258a and a tapering lower region 258b. Guide means are provided to guide movement of the cradle 258 relative to the wall 244. These guide means may take the form of discrete projections 260 provided on the cradle 258 at the upper region 258a and which extend into recesses 262 in the wall 244. Cradle 258 includes a seat 264 for receiving the heating means 254 and the associated probe 256. Biasing means, such as springs 280, are provided between the upper edge of the cradle 258 and a component fixed to the wall 244 or a portion of the housing 242.

Figure 10:
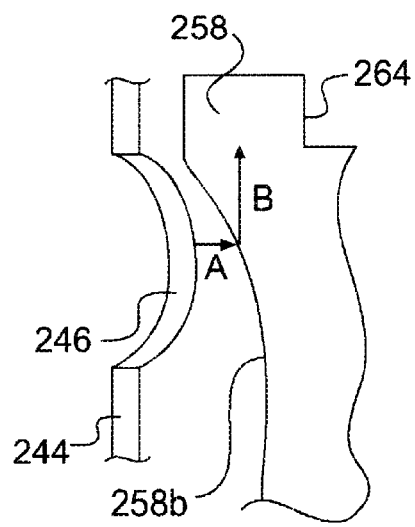
FIG. 10 is a partial view of the embodiment of the instrument shown in FIG. 8.

The tapering lower region 258b of the cradle 258 is positioned inward of the depressed region 248 as shown in FIG. 10. The slope or curvature of the tapering lower region 258b is designed to convert an inwardly applied force on the depressed region 248 (represented by arrow A in FIG. 10) into an upward force (represented by arrow B in FIG. 10) causing the cradle 258 to move upward against the bias provided by springs 280 and thus the probe 256 to move out of the housing 242. To limit the extension of the probe 256 beyond a design limit, the projections 260 and recesses 262 are constructed to cause the projections to abut against the end of the recesses once the probe 256 reaches a predetermined maximum extension from the housing 242. The lower edge of the cradle 258 may be flared outward as shown to thereby assist in limiting the extension of the probe 256.

Figure 11:
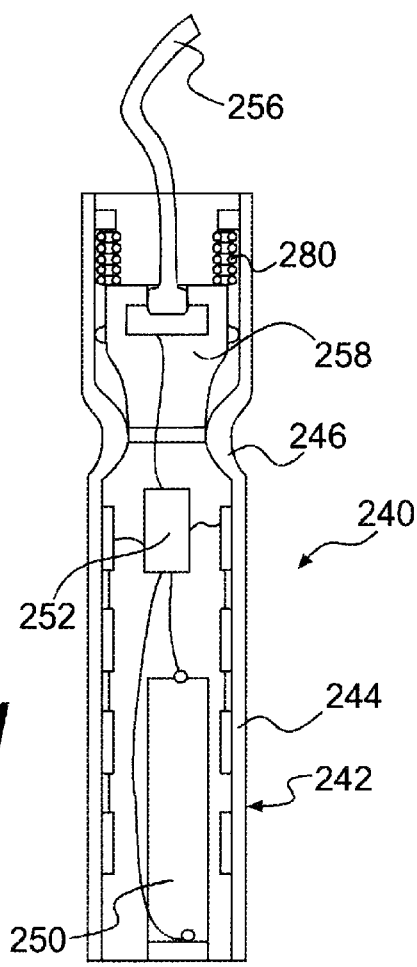
FIG. 11 is a cross-sectional view of the instrument shown in FIG. 8 taken along the line 8A—8A when the instrument is in its operative position.

In use, the practitioner grasps the instrument 240 and while applying pressure to wall 244, depresses region 248. The pressure applied to wall 244 causes the pressure sensors 246 to register the application of pressure and direct appropriate signals to the control unit 252. Control unit 252 then allows for electrical flow to the heating means 254 to heat the probe 256. The inward depressing of the region 248 results in a force being exerted against the lower region 258b of the cradle 258 and as a result of the taper provided to this region, the cradle 258 moves upward. In this manner, the probe 256 is moved upward out of the housing 242 to an operative position (as shown in FIG. 11). The probe 256 is maintained in its operative position so long as pressure is applied to the depressed region 248. Once pressure is released, the biasing force of springs 280 will cause the cradle to move downward and thus the probe 256 to retreat back into the housing 242.

It is possible to provide a lock for locking the probe 256 in its operative position to eliminate the need to continually apply force to the region 248 instead of region 248 being depressed, it is sufficient that region is soft and inwardly depressible, i.e., while the remaining portions of the housing 242 are made of a rigid material, region 248 may be made of rubber to enable the exertion of a force against the cradle 258.

Figure 12:
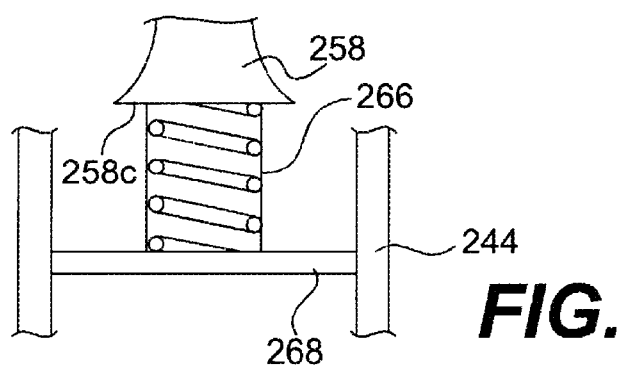
FIG. 12 is a view of a biasing means for use in the instrument of FIG. 8.

FIG. 12 shows an alternative biasing means for exerting a downward force urging the cradle 258 into the housing 242, i.e., instead of springs 280. In this embodiment, the lower edge 258c of the cradle 258 is coupled by biasing means, such as a compression spring 266, to a component 268 of the instrument fixed relative to the wall 244. Spring 266 thus provides a resistive force to the outward extension of the probe 256 from the housing 242 and a force urging the probe 256 back into the housing, indirectly through forces exerted on the cradle 258.

It will be understood that numerous modifications and substitution can be made to the above-described embodiments without deviating from the scope and spirit of the invention. Accordingly, the above-described embodiments are intended for the purpose of illustration and not as limitation.

The preferred embodiments of the invention are described above and unless specifically noted, it is the applicants' intention that the words and phrases in the specification and claims be given the ordinary and accustomed meaning to those of ordinary skill in the applicable art9s). If applicants intend any other meaning, they will specifically state they are applying a special meaning to a word or phrase.

Likewise, applicants' use of the word "function" here is not intended to indicate that the applicants seek to invoke the special provisions of 35 U.S.C. §112, sixth paragraph, to define their invention. To the contrary, if applicants wish to invoke the provisions of 35 U.S.C. §112, sixth paragraph, to define their invention, they will specifically set forth in the claims the phrases "means for" or "step for" and a function, without also reciting in that phrase any structure, material or act in support of the function. Moreover, even if applicants invoke the provisions of 35 U.S.C. §112, sixth paragraph, to define their invention, it is the applicant' intention that their inventions not be limited to the specific structure, material or acts that are described in the preferred embodiments herein. Rather, if applicants claim their inventions by specifically invoking the provisions of 35 U.S.C. §112, sixth paragraph, it is nonetheless their intention to cover and include any and all structure, materials or acts that perform the claimed function, along with any and all known or later developed equivalent structures, materials or acts for performing the claimed function.

We claim:

1. An apparatus for use in obturating a root canal, comprising
   a first member comprising
      an elongate frame,
      a heatable probe mounted to said frame to project outward from said frame and adapted for insertion into or into proximity of the root canal, and
      at least one pressure sensor arranged to detect application of external pressure on said frame, said at least one pressure sensor being coupled to said probe such that said probe is heated upon the detection of the application of pressure on said frame, and
   a second member for covering said probe, said second member being attachable to said first member in a position in which said second member covers said probe and movable from said position to expose said probe.

2. The apparatus of claim 1, wherein said second member is a retractable cover connected to said first member and having a first position in which said cover covers said probe and a second retracted position in which said probe is exposed.

3. The apparatus of claim 2, further comprising
   displacement means for enabling said cover to move between the first position and the second position.

4. The apparatus of claim 3, wherein said displacement means comprise cooperating threads arranged on an outer periphery of said first member and on an inner surface of said cover.

5. The apparatus of claim 1, wherein said first member is a cylindrical tube, said at least one pressure sensor being arranged on an inner surface of said tube.

6. The apparatus of claim 1, wherein said first member is a cylindrical tube having a wall, said at least one pressure sensor being embedded in said wall.

7. The apparatus of claim 1, further comprising
   heating means arranged in connection with said frame for heating said probe, and
   power means arranged in connection with said heating means.

8. The apparatus of claim 7, further comprising
   control means for controlling said heating means such that heating of said probe by said heating means is regulated, said control means being coupled to said at least one pressure sensor and directing said heating means to heat said probe when the application of external pressure on said frame is detected by said at least one pressure sensor.

9. The apparatus of claim 7, wherein said at least one pressure sensor is arranged to provide a signal indicative of the magnitude of the external pressure, further comprising
   control means for controlling said heating means such that heating of said probe by said heating means is regulated, said control means being coupled to said at least one pressure sensor and directing said heating means to heat said probe when the application of external pressure on said frame is detected by said at least one pressure sensor and to a variable temperature based on the magnitude of the external pressure.

10. The apparatus of claim 1, wherein said second member is a cover slidably connected to said first member such that said cover is slidable between a position in which said cover covers said probe and a position in which said probe is exposed.

11. The apparatus of claim 10, wherein said cover comprises axially extending channels and a respective slot at each end of each of said channels, said slots extending circumferentially around at least a portion of an inner surface of said cover, said first member including projections at an upper end, each of said projections being slidable within a respective one of said channels and slots associated with said channel.

12. The apparatus of claim 1, wherein said at least one pressure sensor comprises a plurality of pressure sensors.

13. The apparatus of claim 1, wherein said frame is a cylindrical sleeve having an inner surface, said at least one pressure sensor being arranged on said inner surface of said sleeve.

14. The apparatus of claim 1, wherein said at least one pressure sensor is spaced from said heatable probe.

15. The apparatus of claim 1, wherein said probe has a curvature at an end distal from said frame.

16. The apparatus of claim 1, wherein said frame is a tube having a cylindrical outer surface, said at least one pressure sensor being arranged to detect the application of external pressure on said cylindrical outer surface.

17. The apparatus of claim 1, wherein said frame is a sleeve having a tubular wall, said at least one pressure sensor being embedded in said wall and arranged to detect the application of external pressure on said wall.

18. The apparatus of claim 1, wherein said at least one pressure sensor is arranged to provide a signal indicative of the magnitude of the external pressure and said probe is heated based on the magnitude of the external pressure.

19. An apparatus for use in obturating root canals, comprising
- a cylindrical housing having an inwardly depressible region,
- a heatable probe adapted for insertion into or into proximity of the root canal, and
- a cradle having a seat in which said probe is received, said cradle being arranged inward of said depressible region of said housing and constructed such that depression of said region causes displacement of said cradle and movement of said probe in an outward direction.

20. The apparatus of claim 19, further comprising
- heating means arranged in said seat of said cradle and in engagement with said probe for heating said probe.

21. The apparatus of claim 19, further comprising
- at least one pressure sensor arranged on said housing for detecting application of external pressure on said housing, said at least one pressure sensor being coupled to said probe such that said probe is heated upon the application of pressure on said housing.

22. The apparatus of claim 21, further comprising
- heating means arranged in engagement with said probe for heating said probe, and
- control means for controlling said heating means such that heating of said probe by said heating means is regulated, said control means being coupled to said at least one pressure sensor and directing said heating means to heat said probe when the application of external pressure on said housing is detected by said at least one pressure sensor.

23. The apparatus of claim 19, wherein said cradle has a wide upper region and a tapering lower region.

24. The apparatus of claim 19, further comprising
- biasing means for exerting a force on said cradle opposing the displacement of said cradle upon application of external pressure on said housing.

25. The apparatus of claim 24, wherein said biasing means comprise springs arranged between an upper edge of said cradle and a fixed portion of said housing.

26. The apparatus of claim 24, wherein said biasing means comprise a compression spring arranged between a lower edge of said cradle and a fixed portion of said housing.

27. The apparatus of claim 19, wherein said cradle includes a tapering region arranged inward of said depressible region of said housing.

28. The apparatus of claim 19, further comprising
- guide means for guiding displacement of said cradle.

29. An apparatus for use in obturating a root canal, comprising
- a first member comprising
  - a frame,
  - a heatable probe mounted to said frame to project outward from said frame and adapted for insertion into or into proximity of the root canal, and
  - at least one pressure sensor for detecting application of external pressure on said first member, said at least one pressure sensor being coupled to said probe such that said probe is heated upon the application of pressure on said first member, and
- a second member for covering said probe, said second member being attachable to said first member in a position in which said second member covers said probe and movable from said position to expose said probe,
- said second member being a retractable cover connected to said first member and having a first position in which said cover covers said probe and a second retracted position in which said probe is exposed.

30. An apparatus for use in obturating a root canal, comprising
- a first member comprising
  - a frame,
  - a heatable probe mounted to said frame to project outward from said frame and adapted for insertion into or into proximity of the root canal, and
  - at least one pressure sensor for detecting application of external pressure on said first member, said at least one pressure sensor being coupled to said probe such that said probe is heated upon the application of pressure on said first member, and
- a second member for covering said probe, said second member being attachable to said first member in a position in which said second member covers said probe and movable from said position to expose said probe,
- said second member being a cover slidably connected to said first member such that said cover is slidable between a position in which said cover covers said probe and a position in which said probe is exposed.

* * * * *